(12) United States Patent
Caicedo et al.

(10) Patent No.: US 9,581,570 B2
(45) Date of Patent: Feb. 28, 2017

(54) DETERMINATION OF THE REMAINING LIFE OF A STRUCTURAL SYSTEM BASED ON ACOUSTIC EMISSION SIGNALS

(75) Inventors: Juan M. Caicedo, Columbia, SC (US); Boris A. Zarate, Columbia, SC (US); Paul H. Ziehl, Irmo, SC (US); Jianguo Peter Yu, Columbia, SC (US)

(73) Assignee: University of South Carolina, Columbia, SC (US)

( * ) Notice: Subject to any disclaimer, the term of this patent is extended or adjusted under 35 U.S.C. 154(b) by 803 days.

(21) Appl. No.: 13/370,664

(22) Filed: Feb. 10, 2012

(65) Prior Publication Data

US 2012/0209538 A1  Aug. 16, 2012

Related U.S. Application Data

(60) Provisional application No. 61/462,965, filed on Feb. 10, 2011.

(51) Int. Cl.
*G01N 29/14* (2006.01)
*G01N 29/04* (2006.01)
*G01N 29/44* (2006.01)

(52) U.S. Cl.
CPC .......... *G01N 29/14* (2013.01); *G01N 29/043* (2013.01); *G01N 29/4472* (2013.01); *G01N 2291/0232* (2013.01); *G01N 2291/0258* (2013.01)

(58) Field of Classification Search
CPC .......... G01N 29/14; G01N 2291/0258; G01N 29/043; G01N 29/4472
USPC .............. 702/39, 42, 181; 703/1, 6
See application file for complete search history.

(56) References Cited

U.S. PATENT DOCUMENTS

| 5,554,810 A * | 9/1996 | Anifrani et al. ................. 73/801 |
| 2005/0107963 A1* | 5/2005 | Campbell ........................ 702/42 |
| 2009/0070048 A1* | 3/2009 | Stothers et al. ................. 702/39 |
| 2010/0161244 A1* | 6/2010 | Ghoshal ................. G01N 29/14 702/35 |

OTHER PUBLICATIONS

J.M. Nichol, A bayesian approach to identifying structural nonlinearity using free decay response: Application to damage detection in composites, Feb. 2010.*
M.S.M. Zain, Acoustic Emission Study of Fatigue Crack Growth in Rail Track Material, Dec. 2010.*
Fady F. Barsoum, Acoustic Emissionb Monitoring and Fatigue Life Prediction in Axially Loaded Notched Steel Specimens, 2009.*
Tomor, "Monitoring masonry arch bridge response to traffic loading using avoustic emission techniques", 2007.*

(Continued)

*Primary Examiner* — Michael Nghiem
*Assistant Examiner* — Peter Ngo
(74) *Attorney, Agent, or Firm* — Dority & Manning, P.A.

(57) ABSTRACT

In accordance with the present disclosure, a method of using acoustic emission data to predict the state of a structural element is described. The method includes capturing acoustic emission data for a structural element. The method further includes predicting the future stress intensity in the structural element using the captured acoustic emission data and calculating the probability of future failure of the structural element using the predicted future stress intensity.

20 Claims, 17 Drawing Sheets

(56) References Cited

OTHER PUBLICATIONS

Beck et al., "Updating Models and Their Uncertainties. I: Bayesian Statistical Framework", Journal of Engineering Mechanics, vol. 124, No. 4, Apr. 1998, pp. 455-461.

Caicedo et al., "Reducing Epistemic Uncertainty Using a Model Updating Cognitive System", Advances in Structural Engineering, 2010 (Special Issue—$5^{th}$ Workshop of Asian-Pacific Network of Centers for Research in Smart Structure Technology (ANCRiSST 2009).

Chapra, Numerical Methods for Engineers, Third Edition, 1998, London: McGraw-Hill.

Chib, "Understanding the Metropolic-Hastings Algorithm", The American Statistician, vol. 49, No. 4, Nov. 1995, pp. 327-335.

Dowling, Mechanical Behavior of Materials: Engineering Methods for Deformation, Fracture and Fatigue, Fracture of Cracked Members, Upper Saddle River, Pearson Prentice Hall, 33.

Foreman et al., "Numerical Analysis of Crack Propagation in Cycle-Loaded Structures", Journal of Basic Engineering, ASME, vol. 89, 1967, pp. 459-464.

Gelman et al., "Inference from Iterative Simulation Using Multiple Sequences", Statistical Science, vol. 7, No. 4, 1992, pp. 457-472.

Gong et al., "Acoustic Emission Monitoring of Steel Railroad Bridges", Materials Evaluation, vol. 50, No. 7, Jul. 1992, pp. 883-887.

Kennedy et al., "Bayesian Calibration of Computer Models," Journal of the Royal Statistical Society. Series B, Statistical Methodology, vol. 63, No. 3, 2001, pp. 425-464.

Paris et al., "A Critical Analysis of Crack Propagation Laws", Transactions of the ASME, Journal of Basic Engineering, Series D, vol. 85, No. 3, 1963, pp. 528-534.

Robert et al., Monte Carlo Statistical Methods, Second Edition, 2004, Springer-Verlag.

Roberts et al., "Fatigue Life Prediction Based on Crack Propagation and Acoustic Emission Count Rates", Journal of Constructional Steel Research, vol. 59, No. 6, Jun. 2003, pp. 679-694.

Weertman, "Rate of Growth of Fatigue Cracks Calculated from the Theory of Infinitesimal Dislocations Distributed on a Plane", International Journal of Fracture Mechanics, vol. 2, No. 2, 1966, pp. 460-467.

Wheeler, "Spectrum Loading and Crack Growth", Journal of Basic Engineering, ASME, vol. 94, No. 1, 1972, pp. 181-186.

Yu et al., "Prediction of Fatigue Crack Growth in Steel Bridge Components Using Acoustic Emission", Journal of Constructional Steel Research, vol. 67, No. 8, Aug. 2011, pp. 1254-1260.

Zarate et al., "Alternative Solutions and Their Probabilities for the Model Updating of Structural Systems, in Civil and Environmental Engineering Department", 2009, University of South Carolina, Columbia, South Carolina.

Zarate et al., "Finite Element Model Updating: Multiple Alternatives", Engineering Structures, vol. 30, No. 12, Dec. 2008, pp. 3724-3730.

Barsoum et al., "Acoustic Emission Monitoring and Fatigue Life Prediction in Axially Loaded Notched Steel Specimens," Journal of Acoustic Emission, vol. 27, Jan.-Dec. 2009, pp. 40-63.

* cited by examiner

Figure 1. Specimen geometry and sensor location

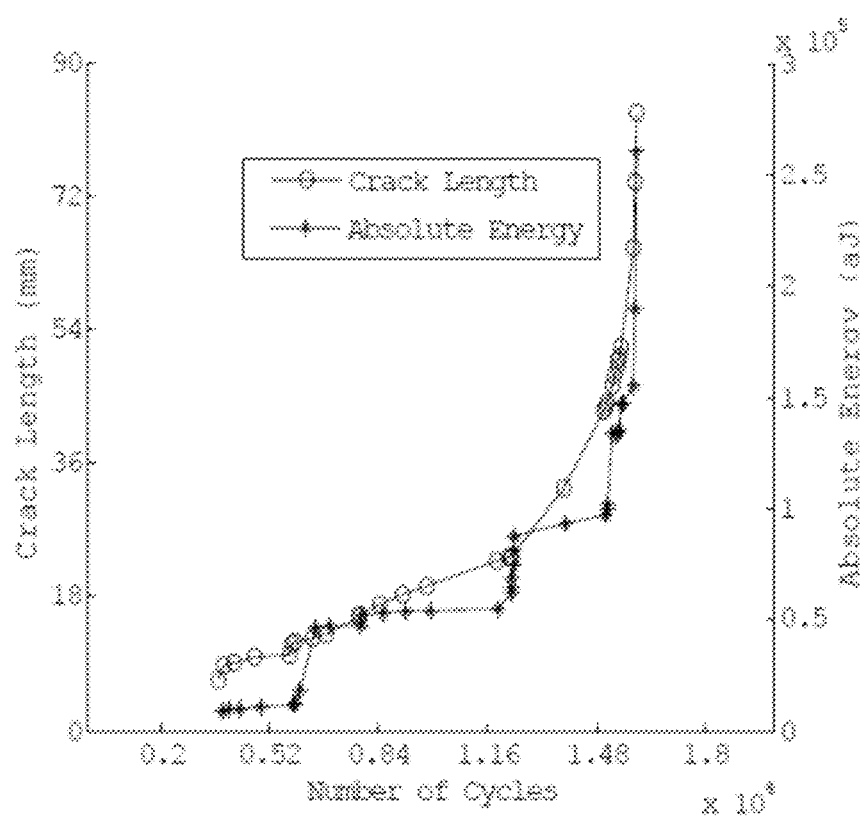
Figure 3. CT1 cumulative absolute energy of the AE signal and measured crack length versus number of cycles

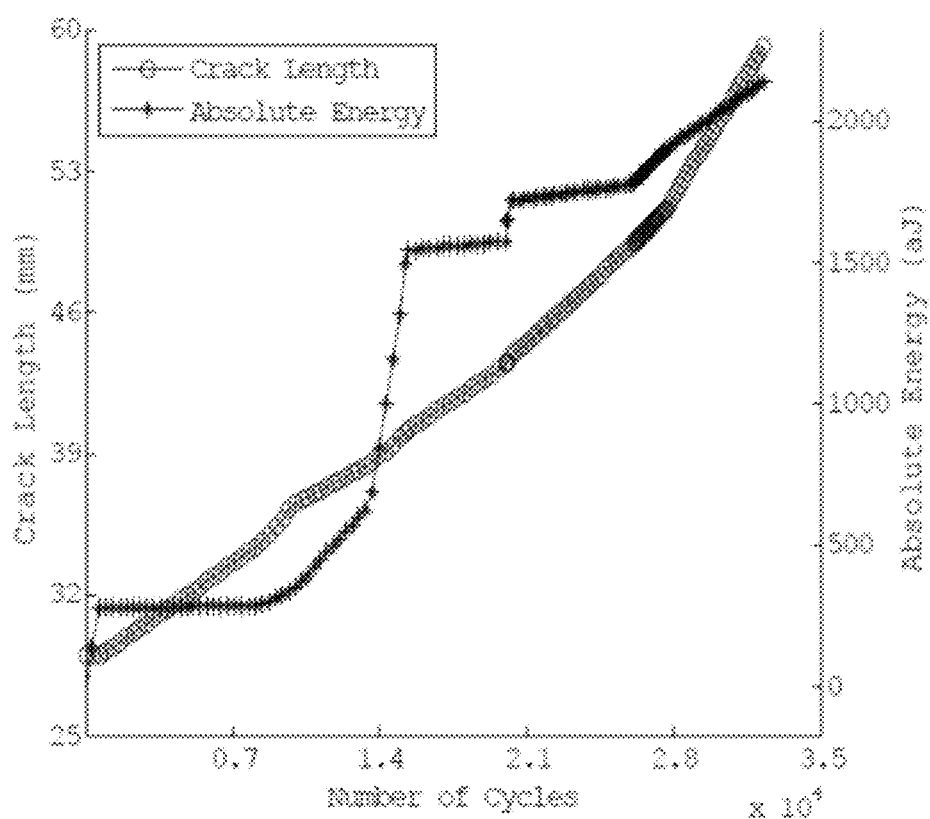
Figure 4. CT2 cumulative absolute energy of the AE signal and measured crack length versus number of cycles

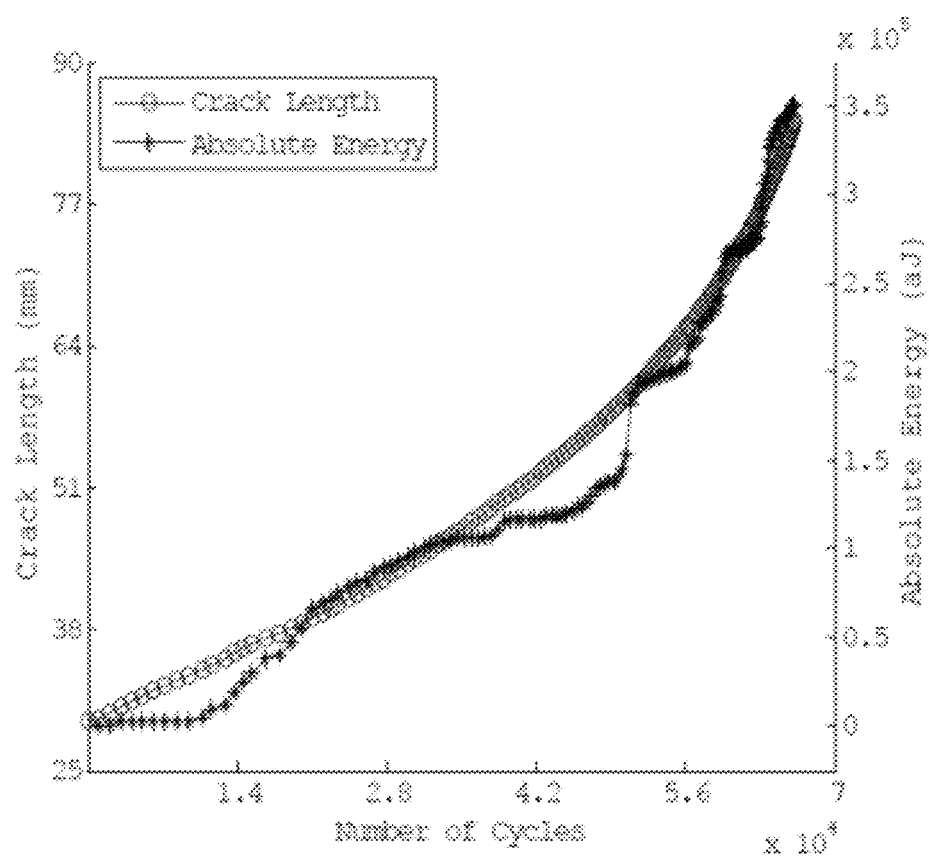
Figure 5. CT3 cumulative absolute energy of the AE signal and measured crack length versus number of cycles

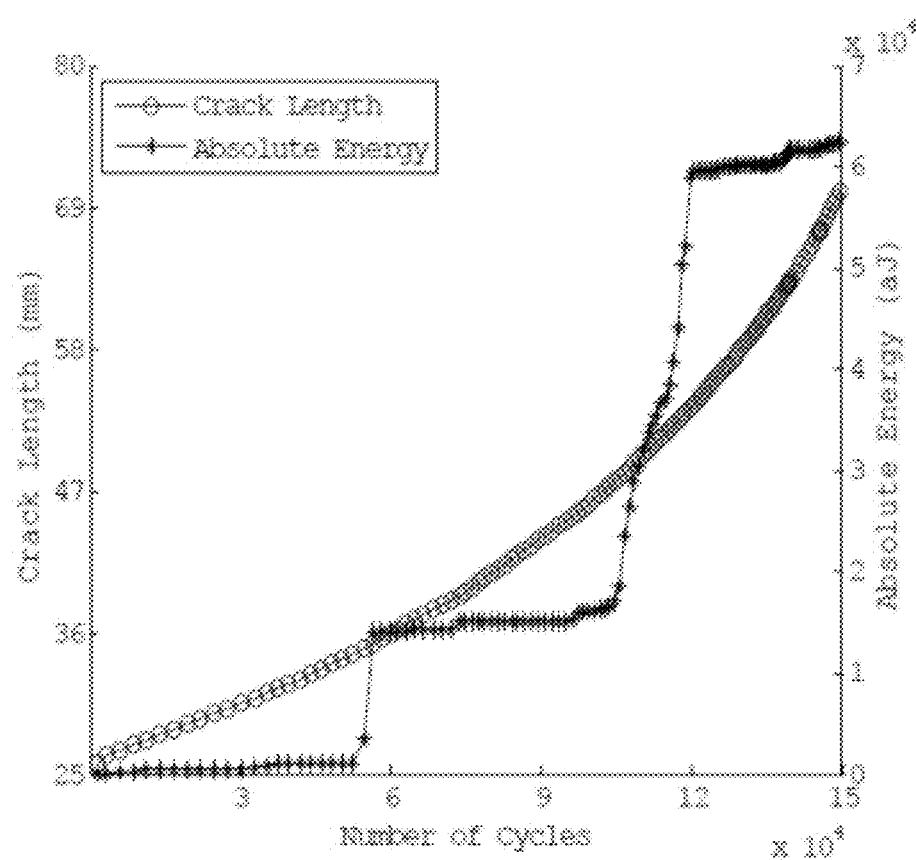
Figure 6. CT4 cumulative absolute energy of the AE signal and measured crack length versus number of cycles

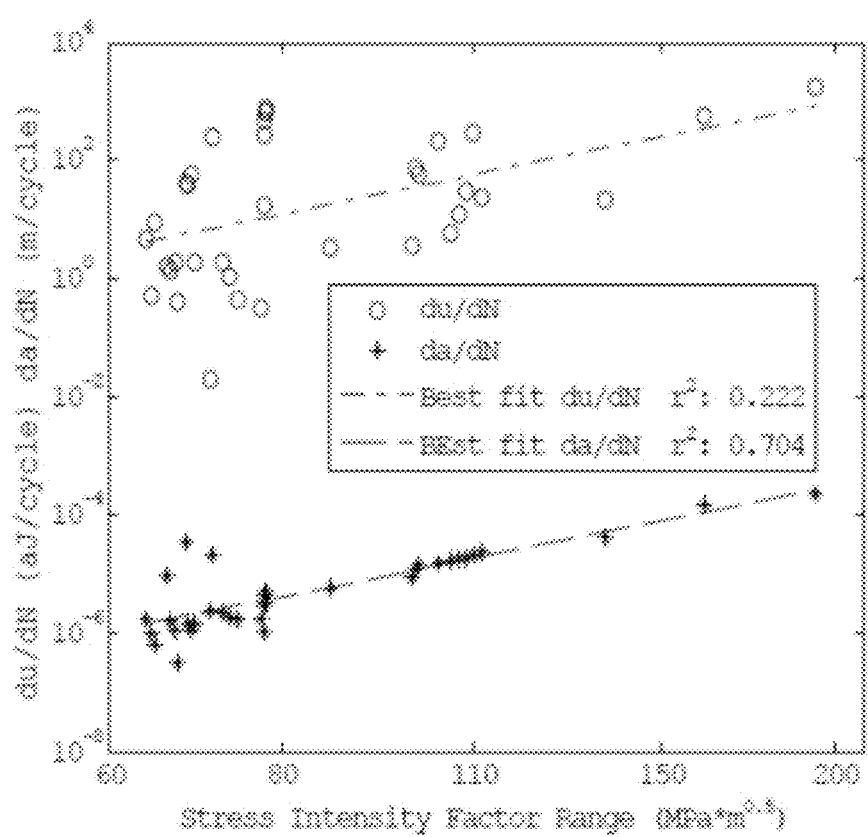
Figure 7. CT1 crack length rate and absolute energy rate versus stress intensity factor range

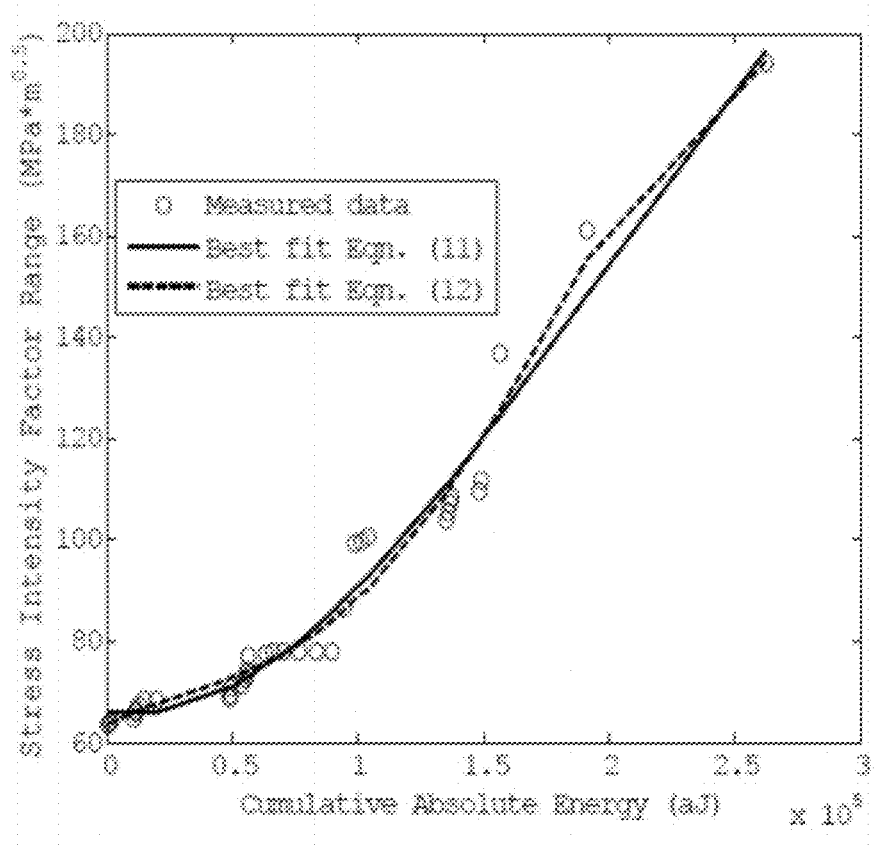
Figure 8. CT1 stress intensity factor range versus cumulative absolute energy

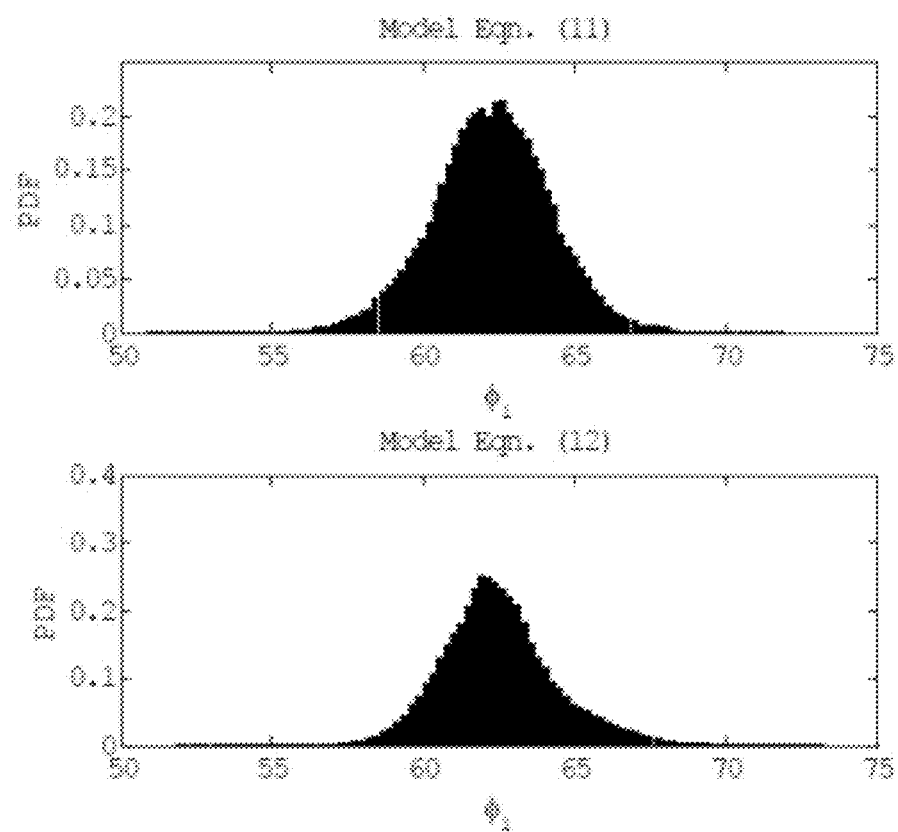
Figure 9. CT1 marginal probability distribution of the stress intensity factor range at the moment of sensor deployment

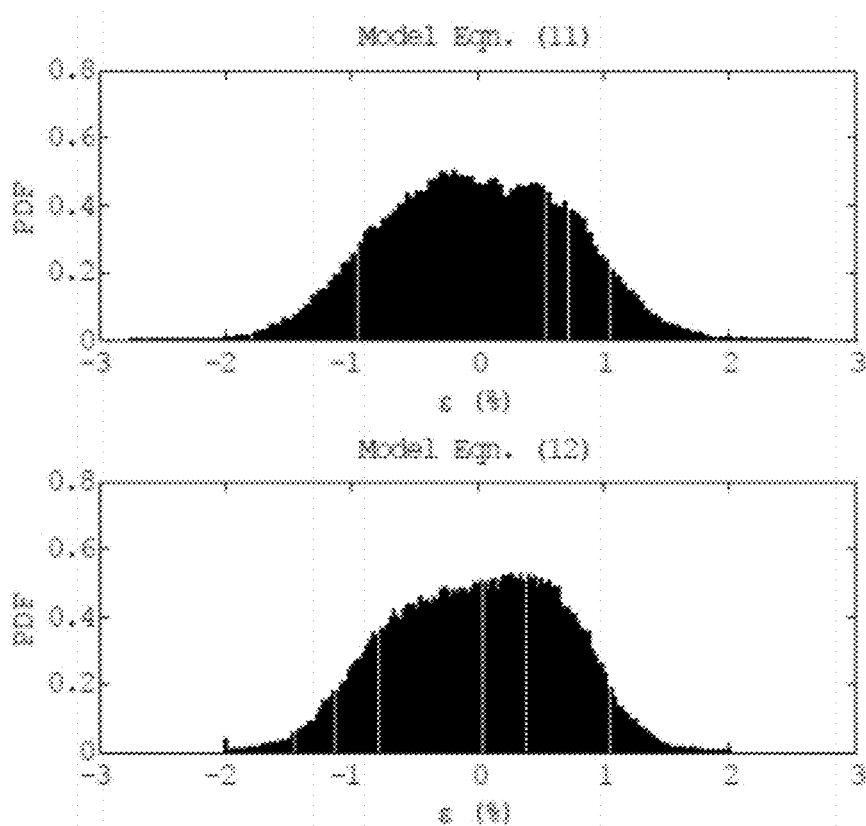
Figure 10. CT1 marginal probability distribution of the error (%)

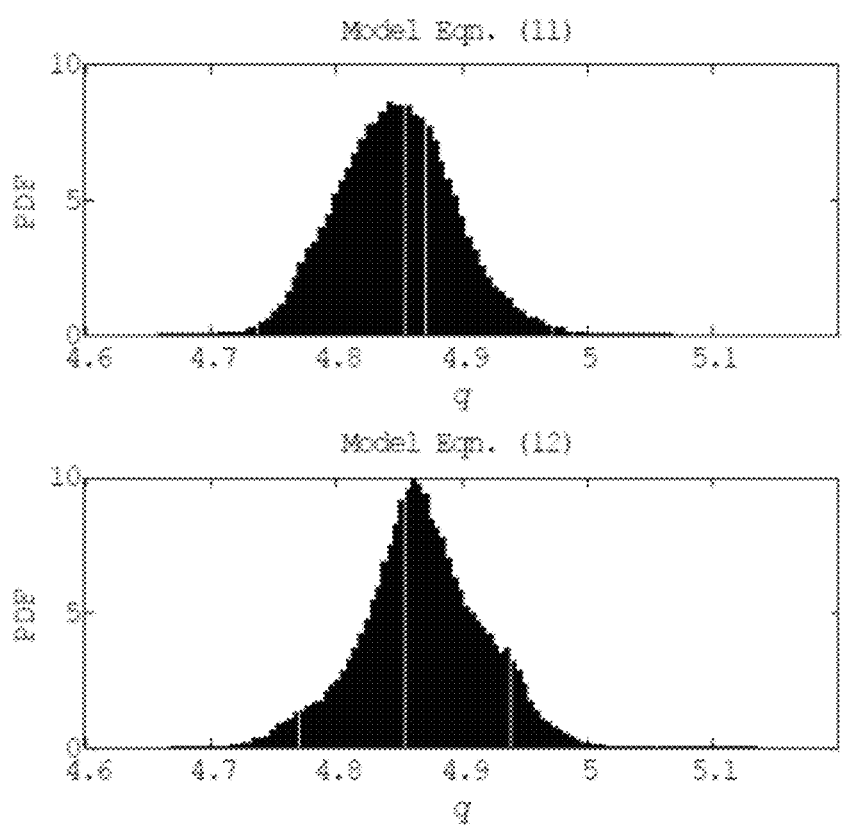
Figure 11. CTI marginal probability distribution of the material constant $q$

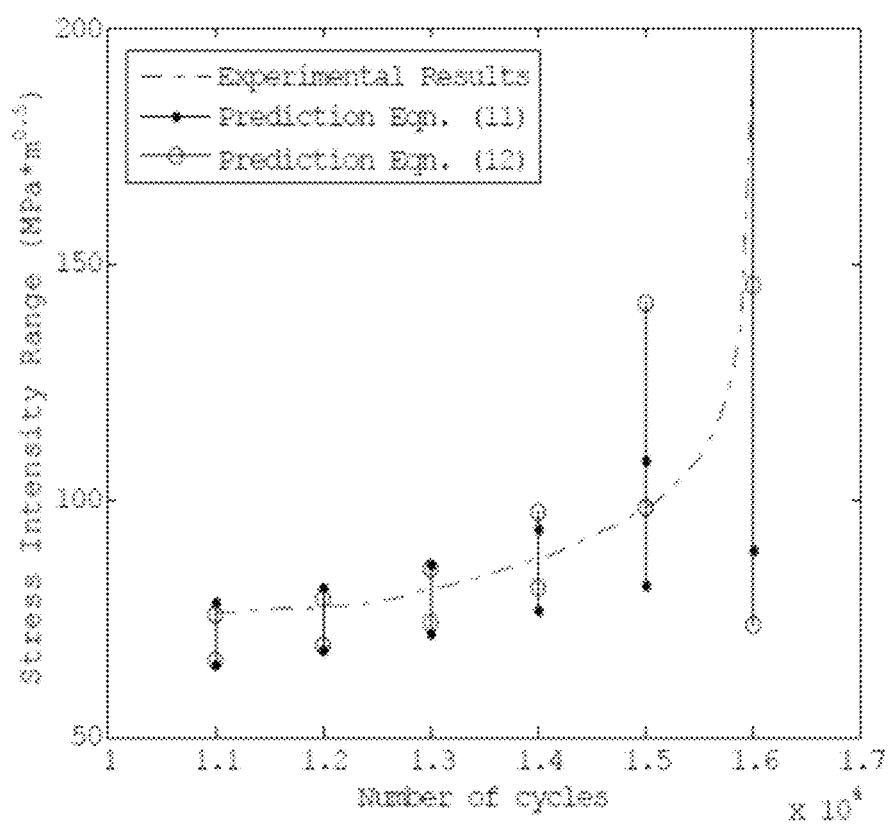
Figure 12. CT1 prognosis at 99 % confidence interval of predicted stress intensity factor range using data from 0 to 10000 cycles

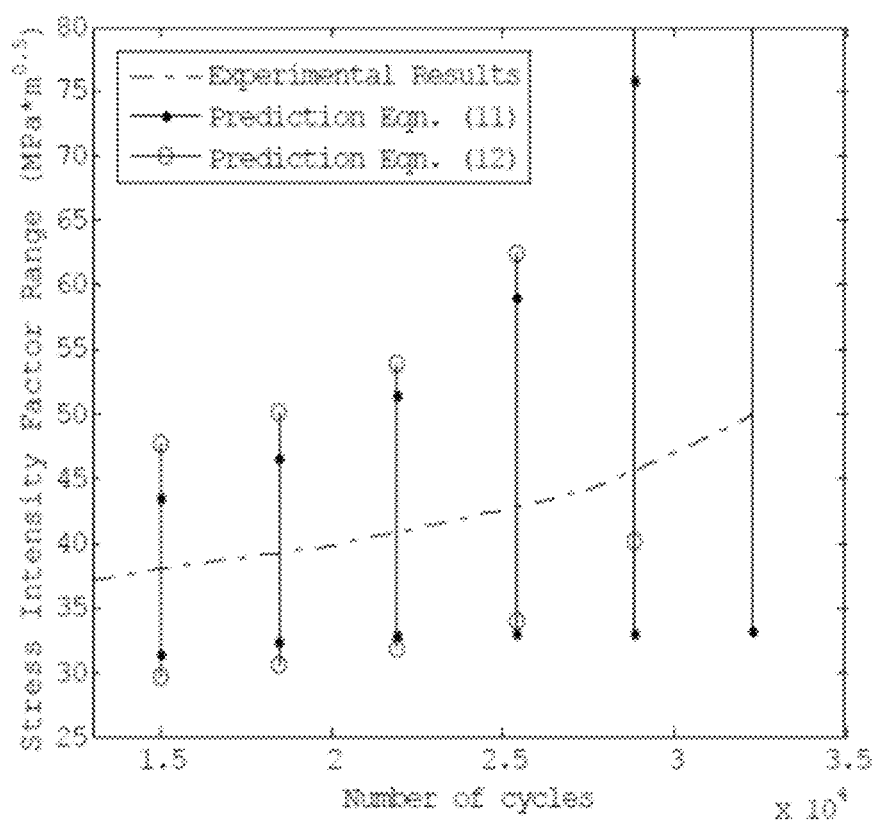
Figure 13. CT2 prognosis at 99 % confidence interval of predicted stress intensity factor range using data from 0 to 14000 cycles

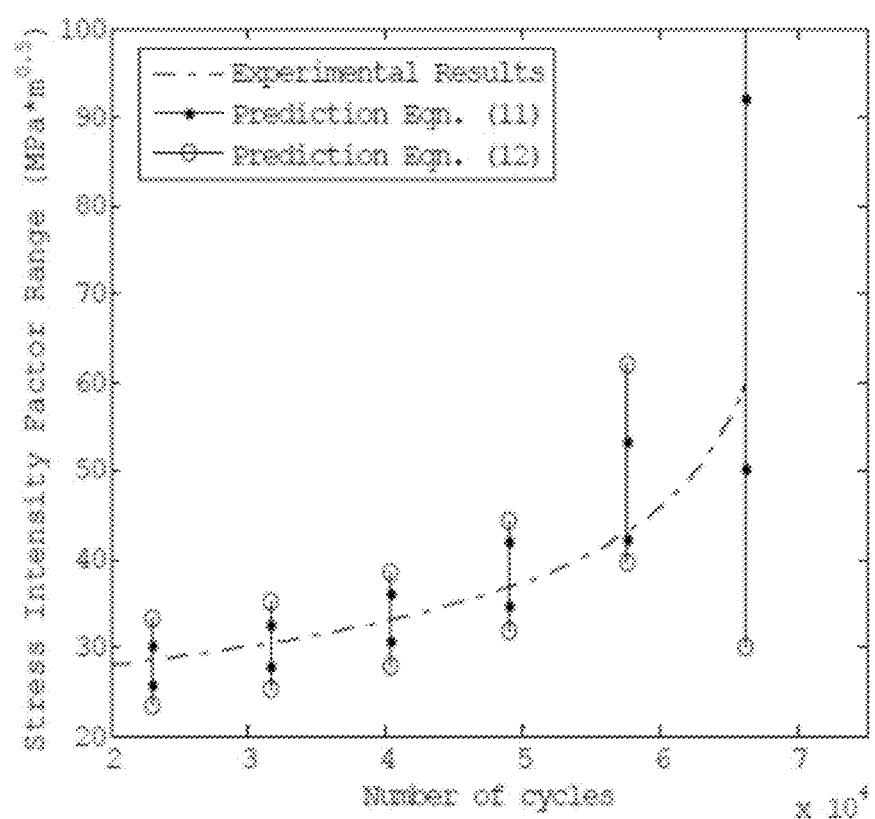
Figure 14. CT3 prognosis at 99 % confidence interval of predicted stress intensity factor range using data up to 22000 cycles

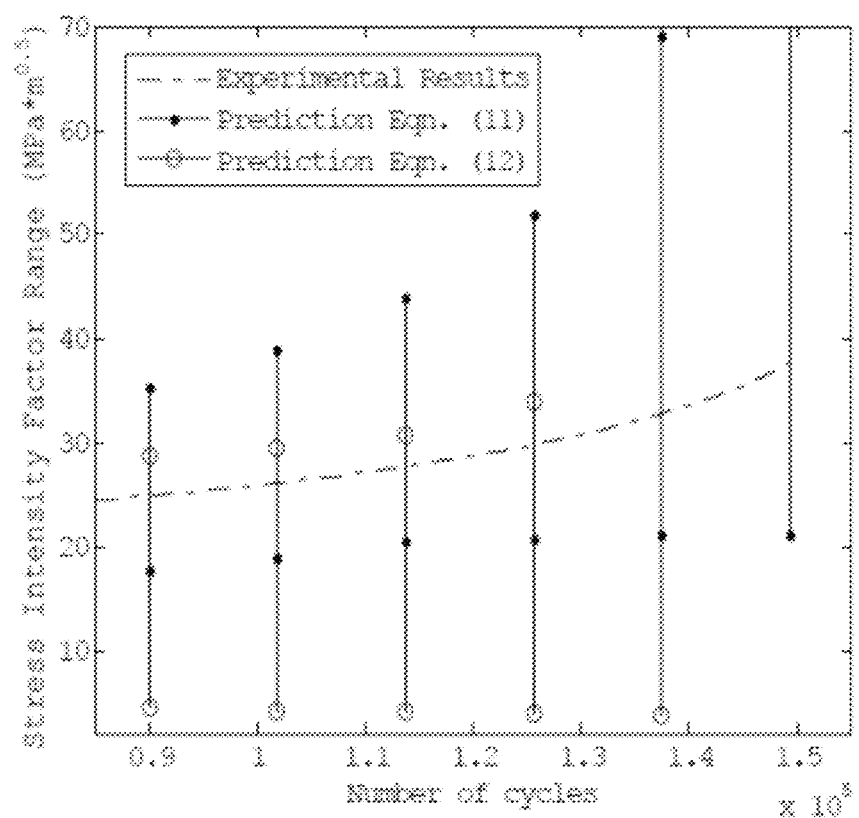
Figure 15. CT4 prognosis at 99 % confidence interval of predicted stress intensity factor range using data up to 89000 cycles

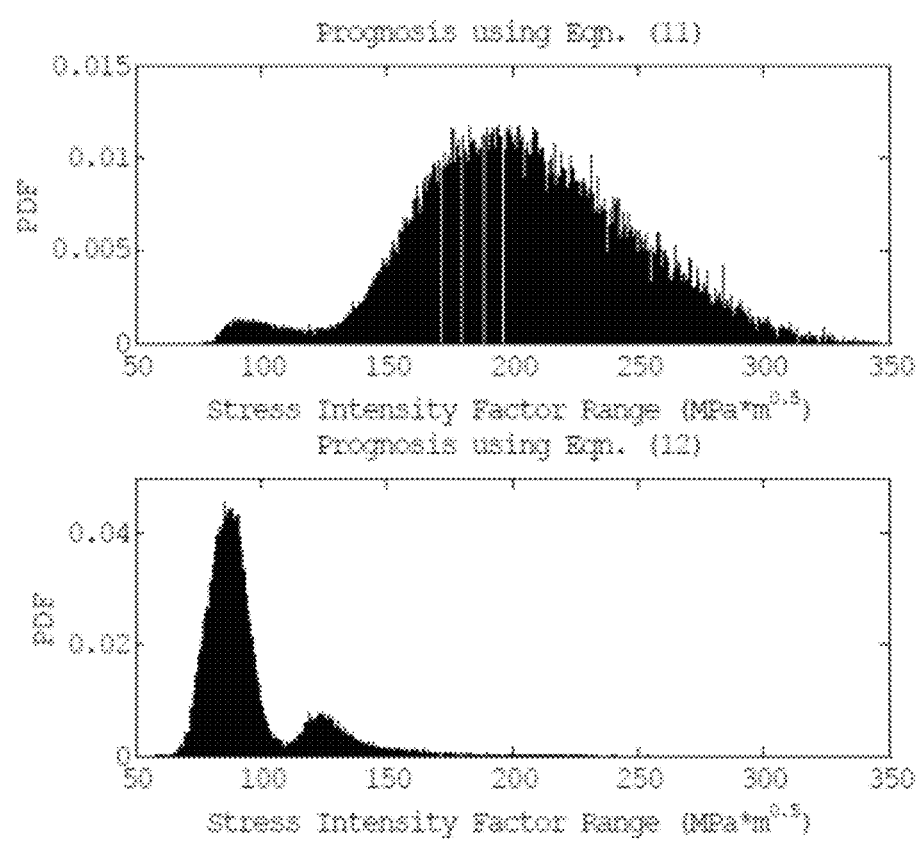
Figure 16. Prognosis at 16000 cycles using the models of Eqn. (11) and Eqn. (12)

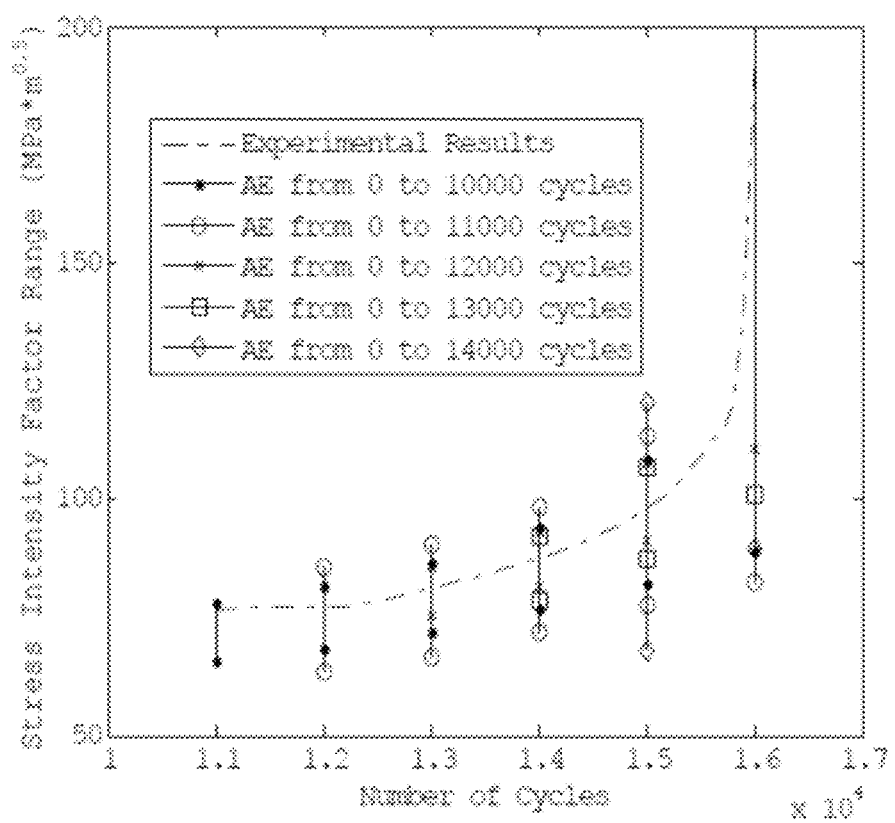
Figure 17. CTI prognosis using the model of Eqn. (11) at 99 % confidence interval of predicted stress intensity factor range using from 0 to 10000, 11000, 12000, 13000 and 14000 cycles

DETERMINATION OF THE REMAINING LIFE OF A STRUCTURAL SYSTEM BASED ON ACOUSTIC EMISSION SIGNALS

PRIORITY INFORMATION

The present application claims priority to U.S. Provisional Patent Application Ser. No. 61/462,965 filed on Feb. 10, 2011, the disclosure of which is incorporated by reference herein.

GOVERNMENT SUPPORT CLAUSE

This invention was made with government support under 70NANB9H9007 awarded by the National Institute of Standards and Technology. The government has certain rights in the invention.

BACKGROUND

Many bridges built in the 1950s and 1960s in the United States are reaching their design life span. According to the ASCE (2009) Report Card bridges are commonly built to last 50 years and the average bridge in the United States is 43 years old. Furthermore, about 15% of the bridges are considered obsolete and are subjected to heavier loads than in the past because of the continuous increase in truck miles and carrying loads. Additionally the Committee on Fatigue and Fracture Reliability of the Committee on Structural Safety and Reliability of the Structural Division ASCE acknowledged that 80 to 90% of the failures in metallic structures are caused by a combination of fatigue and fracture (ASCE 1982). These statistics highlight the importance of condition assessment, specifically the monitoring of cracks in steel structural elements. Studies performed by the Federal Highway Administration show that bridge inspections are performed mainly through visual inspections with little use of other non-destructive techniques. Visual inspections are inexpensive, however are subjective and highly dependent of the experience of the inspector.

Many non-destructive techniques for the monitoring of crack growth have been proposed in the literature. X-rays, electric inspection, acoustic emission (AE), and dye penetrants have been utilized to assess the fatigue life of structural elements. AE is the most used non-destructive technique for monitoring bridges and other large structures.

AE uses a broad band of high frequency (ultrasonic 100 kHz to 1 MHz) sound waves typically Rayleigh (surface) and Lamb (plate) waves. These waves are created by a sudden release of energy, which can be either caused by a piezoelectric transducer (active AE) or events in the material such as phase transformation, grain boundary slip, and the growth of a crack (passive AE). Active ultrasound has been used for the detection and image of cracks on plates. An oscillatory voltage at the piezoelectric coupling sensor creates a Lamb wave that travels through the material and is affected by the surface cracks. The characteristics from the received signal allow locating and imaging cracks at the surface material. The methodology has been validated using different methods such as guided waves in pitch-catch, pulse-echo, or high frequency impedance spectrum method in different materials like steel, aluminum, and fiber reinforced polymers. Passive AE based on the transient elastic waves generated by the release of energy at crack growth has been proposed for the monitoring of cracks. It is known that a portion of the energy released at the instant of crack growth is dissipated in the form of elastic waves and heat. The premise is that AE features (e.g. number of counts that the signal is above some threshold level, absolute energy, or signal strength) are an indication of the energy released, which can be used to estimate the current state of the crack using fracture mechanics theory. In practice this is very challenging because there is not a theoretical relationship between AE features and the fracture mechanics parameters even though that studies suggest that AE rate increases as the crack growth rate increases. The relationships are difficult to apply to all structural element geometries, because each structural member of every bridge is different and most of them contain complex geometries. A methodology that estimates the stress intensity factor range without the need of knowing the structural member geometry would be appropriate for damage identification and prognosis of steel bridges.

Ideally, bridges should have a real-time condition assessment and monitoring system that monitors and estimates the probability of collapse of a particular structure based on the state of crack growth of critical structural members. Ideally, this process should be performed automatically and with as little human intervention as possible. The information should be transferred to bridge engineers to support decisions on maintenance and retrofit. However, the state of the art on crack growth monitoring using AE is not at that point yet, because the current relationships between sensed data and physical structural parameters are difficult to apply to operational bridges. In addition most of the Bayesian methodologies available in the literature are based on crack length measurements which are difficult to obtain.

SUMMARY

Objects and advantages of the invention will be set forth in part in the following description, or may be obvious from the description, or may be learned through practice of the invention.

In accordance with the present disclosure, a method of using acoustic emission data to predict the state of a structural element is described. The method includes capturing acoustic emission data for a structural element. The method further includes predicting the future stress intensity in the structural element using the captured acoustic emission data and calculating the probability of future failure of the structural element using the predicted future stress intensity.

Other exemplary implementations of the present disclosure are directed to systems, apparatus, computer-readable mediums, devices, and user interfaces for predicting the state of a structural element.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which:

FIG. 3 illustrates a graph showing CT1 cumulative absolute energy of the AE signal and measured crack length versus number of cycles in accordance with certain aspects of the present disclosure;

FIG. 4 illustrates a graph showing CT2 cumulative absolute energy of the AE signal and measured crack length versus number of cycles in accordance with certain aspects of the present disclosure;

FIG. 5 illustrates a graph showing CT3 cumulative absolute energy of the AE signal and measured crack length versus number of cycles in accordance with certain aspects of the present disclosure;

FIG. 6 illustrates a graph showing CT4 cumulative absolute energy of the AE signal and measured crack length versus number of cycles in accordance with certain aspects of the present disclosure;

FIG. 7 illustrates a graph showing CT1 crack length rate and absolute energy rate versus stress intensity factor range in accordance with certain aspects of the present disclosure;

FIG. 8 illustrates a graph showing CT1 stress intensity factor range versus cumulative absolute energy in accordance with certain aspects of the present disclosure;

FIG. 9 illustrates a graph showing CT1 marginal probability distribution of the stress intensity factor range at the moment of sensor deployment in accordance with certain aspects of the present disclosure;

FIG. 10 illustrates a graph showing CT1 marginal probability distribution of the error (%) in accordance with certain aspects of the present disclosure;

FIG. 11 illustrates a graph showing CT1 marginal probability distribution of the material constant q in accordance with certain aspects of the present disclosure;

FIG. 12 illustrates a graph showing CT1 prognosis at 99% confidence interval of predicted stress intensity factor range using data from 0 to 10000 cycles in accordance with certain aspects of the present disclosure;

FIG. 13 illustrates a graph showing CT2 prognosis at 99% confidence interval of predicted stress intensity factor range using data from 0 to 14000 cycles in accordance with certain aspects of the present disclosure;

FIG. 14 illustrates a graph showing CT3 prognosis at 99% confidence interval of predicted stress intensity factor range using data from 0 to 22000 cycles in accordance with certain aspects of the present disclosure;

FIG. 15 illustrates a graph showing CT4 prognosis at 99% confidence interval of predicted stress intensity factor range using data up to 89000 cycles in accordance with certain aspects of the present disclosure;

FIG. 16 illustrates a graph showing prognosis at 16000 cycles using the models of Eqn. (11) and Eqn. (12) in accordance with certain aspects of the present disclosure; and FIG. 17 illustrates a graph showing CT1 prognosis using the model of Eqn. (11) at 99% confidence interval of predicted stress intensity factor range using from 0 to 10000, 11000, 12000, 13000 and 14000 cycles in accordance with certain aspects of the present disclosure.

DETAILED DESCRIPTION

Figure 1:
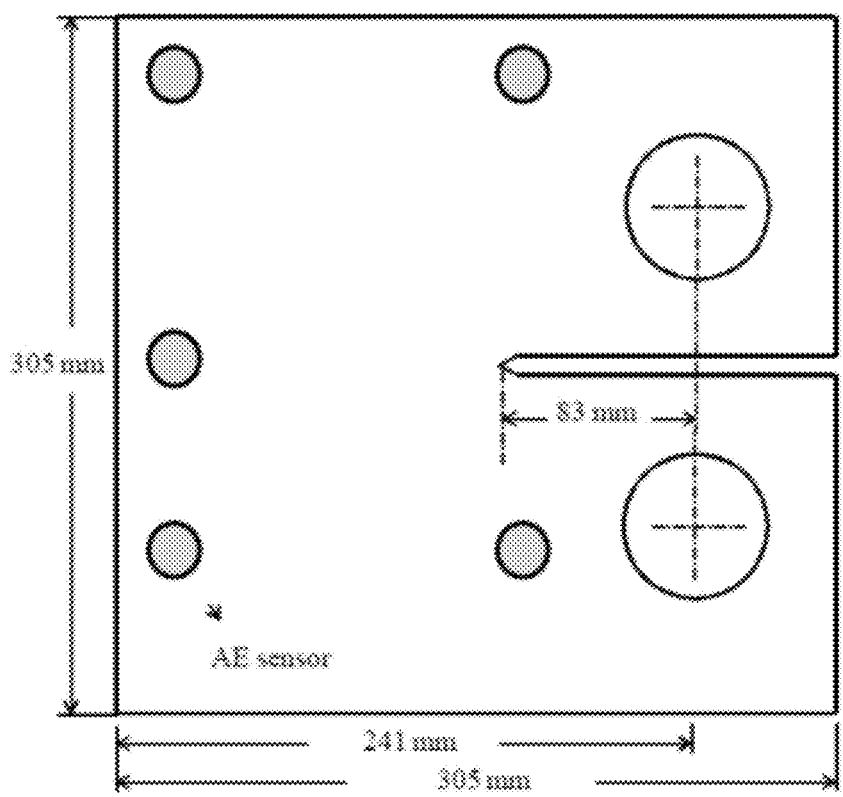
FIG. 1 illustrates specimen geometry and sensor location in accordance with certain aspects of the present disclosure.

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

The present disclosure provides a framework to monitor and predict probabilistically the stress intensity factor range using AE without the need of knowing the geometry of the structural member or the load applied. The absolute energy of the AE signal is correlated probabilistically to the stress intensity factor range of the structural element at the crack tip. This permits predicting failure in the structural member to allow bridge owners to schedule preventive maintenance or retrofit. The methodology of the present disclosure includes two main parts: i) a model updating component that uses Bayesian model updating to determine the posterior probability distribution of the fatigue model parameters, and ii) a prognosis component that uses this posterior distribution to predict the stress intensity factor range as a function of the number of cycles through Markov Chain Monte Carlo (MCMC). Four distinctive uncertainty sources are considered in this fatigue life prediction framework: i) measurement errors, which include the uncertainty in the AE measurements, ii) crack growth modeling errors that come from the numerical models involved such as the Paris law equation, the stress intensity factor equation that accounts for loading and geometric conditions, and other numerical errors involved in the calculations, iii) unknown loading conditions, and iv) unknown material properties (i.e. material constants used in the Paris law).

In accordance with the present disclosure, the equation of the stress intensity factor that includes geometry and loading conditions is considered uncertain itself. This allows the use of the methodology to problems where the stress intensity factor equation is not necessarily known. The framework described herein is validated using numerical and experimental data from a compact tension specimen under cyclic loading.

In elastic materials the available potential energy for crack extension is known as G, which can be written as:

$$G = \frac{K^2}{E'} \quad (1)$$

where K, is the stress intensity factor and E' is the elasticity modulus in case of plane stress. For elastic-plastic materials, the concept of the J-integral serves as a measure of the intensity of the crack tip strain field. For elements under cyclic loading, ΔJ has been proposed by changing the derivation of the J-integral and locating the origin at zero stress and strain from the loading branch of the cyclic curve. In the case in which the plastic region around the crack tip is small compared to the dimensions of the element (small scale yielding), ΔJ approaches to G as $$\Delta J = \frac{\Delta K^2}{E'} \quad (2)$$

where ΔK is the stress intensity factor range.

A relationship has been developed expressing the energy release during crack extension $$\Delta u = \frac{\Delta K^2 D}{E'(1-R)^2} t \Delta a \quad (3)$$

where, t is the specimen thickness, D is a material constant, R is the ratio between the minimum and the maximum loads, and $\Delta a$ is the crack length growth during the loading cycle. Thus, the energy released rate with respect to the number of cycles du/dN can be calculated as $$\frac{du}{dN} = \frac{\Delta K^2 D}{E'(1-R)^2} t \frac{da}{dN} \quad (4)$$

where da/dN is the derivative of the crack length (a) with respect to the number of cycles. Fatigue crack growth can be modeled as a function of the stress intensity factor range using the Paris law given by $$\frac{da}{dN} \propto \Delta K^m \quad (5)$$

where, m, is a material constant. Using Eqn (5) in Eqn (4) and considering that the R, E' and D are constant for stage II under Paris law, the cumulative energy is proportional to the stress intensity range factor:

$$\frac{da}{dN} \propto \Delta K^q \quad (6)$$

where, q, is a material constant. Eqn. (6) is similar to the equations that express the AE number of counts rate as a function of the stress intensity factor range.

Assuming that the energy of the acoustic emission signal, $u_{AE}$ is proportional to the energy released, u, the number of cycles, N, can be obtained by integrating Eq (6) as $$N = \int_{u_{AE_i}}^{u_{AE_f}} \frac{du_{AE}}{B \Delta K^q} \quad (7)$$

where, $u_{AEi}$, $u_{AEf}$ are the initial and final accumulative energy captured by the acoustic emission sensor, and B is a proportionality material constant given by the slope of the logarithmic AE per cycle versus stress intensity range curve. Notice that Eq. (7) cannot be solved analytically, the integration is performed numerically. The final accumulative energy of the acoustic emission signal for a specific number of cycles is found from Eq. (7) using the Newton-Raphson method.

The stress intensity factor range can be estimated for a compact tension specimen using the crack length measurements $$\Delta K = Fp \frac{Pmax - Pmin}{t\sqrt{b}} \quad (8)$$

where, Pmax, is the maximum applied load, Pmin, is the minimum applied load, t, is the specimen thickness, b, is the specimen width, and Fp is given by the equation (a≥0.2)

$$Fp = \frac{2+a}{(1-a)^{3/2}}(0.886 + 4.64a - 13.33a^2 + 14.72a^3 - 5.6a^4) \quad (9)$$

where $$a = \frac{a}{b} \quad (10)$$

From a prognosis point of view Eq. (8) is not ideal because it requires the knowledge of the maximum and minimum load as well as the geometry of the specimen. The present disclosure models the stress intensity factor range as a stochastic process, eliminating the need to know the values of load and geometry characteristics. Furthermore, the stress intensity factor range is modeled as a function of AE activity. Two different equations model the stress intensity factor range as a function of the AE absolute energy $$\Delta K = \phi_1 + \phi_2 u^{\phi_3} \quad (11)$$

$$\Delta K = \phi_1 + \phi_2 u + \phi_3 u^2 + \phi_4 u^3 \quad (12)$$

The parameters $\Phi = [\phi_1, \phi_2, \phi_3, \ldots]$ are non-physical parameters that allow the technique to be applied to the case where measurements of the compact tension (CT) specimen are not known. Furthermore, such equations could be used for other geometries (not CT specimens).

The present disclosure updates the probability distribution of unknown parameters describing the stress intensity factor range and material properties based on experimental data. The probability distribution of the updated parameters stays constant in time and the stress intensity factor range can be predicted based on these parameters. The framework is based on the assumption that number of cycles and the absolute energy of the AE measurements are available. The number of loading cycles should be counted from the moment that the AE sensors are deployed and the previous loading history of the structure is not needed. The number of cycles can be estimated in a bridge by either counting vehicles, or using strain gages, accelerometers, or a combination thereof.

Probability is used to model uncertainty. Probability represents the degree of knowledge on the updating variables, different from the most usual frequency interpretation. A chosen model (e.g. an equation such as Eqn. (6), or a finite element model) can be represented by M, which is a function of some modeling parameters $\Theta$ (i.e. range of load, material properties B and q, etc), and its outcome is a numeric simulation of the experimental observations (i.e. acoustic emission, accelerations, etc) obtained from the structure, D. Then the Bayes' theorem can be written in this context, as $$P(\Theta|D,M) \propto P(D|\Theta,M) P(\Theta|M) \quad (13)$$

where, $P(\Theta|D,M)$ is the posterior probability distribution of the parameters $\Theta$ for the chosen model M, after being updated with the experimental data D, $P(\Theta|M)$, is the prior probability distribution of the parameters $\Theta$ for the chosen model M, and $P(D|\Theta,M)$ is the likelihood of the experimental measurement D, given the vector of parameters $\Theta$, and the model M. A Gaussian distribution is assumed to represent the likelihood as $$P(D|\Theta, M) \propto \prod_{j=1}^{n} \exp\left(-\frac{1}{2}\left(\frac{u_{AE_j}^{id} - u_{AE_j}^{cp}(\Phi, B, q) - \varepsilon_j}{\sigma_j^{u_{AE}}}\right)^2\right) \quad (14)$$

where, n is the number of accumulative AE data measurements at different number of cycles, $u_{AE_j}^{id}(\Theta)$ the j-th measured cumulative absolute energy of the AE signal, $u_{AE_j}^{cp}(\Theta)$ is the j-th computed cumulative absolute energy, $\epsilon_j$ is the modeling error of the j-th cumulative absolute energy of the AE signal, and $\sigma_j^{u_{AE}}$ is the standard deviation of the difference between the j-th measured and the j-th computed cumulative absolute energy of the AE signal for the same number of cycles. The error $\epsilon_j$ evaluates the behavior of the numerical model of Eqn. (7) in representing the experimental data obtained. This error is normalized with respect to the experimental measurements, $u_{AE_j}^{id}$ resulting in the parameter, $\epsilon$. Therefore, large errors would show that the numeric model cannot represent the physical phenomena being modeled assuming the error in the measured data is low.

The prior distribution represents the engineering judgment on the updating variables and its purpose is to include the existing knowledge prior to the experimental observations. In case that there is not any prior knowledge available a non-informative distribution can be used. The uniform distribution is used herein. Non informative distributions are required for the parameters that describe the stress intensity factor range since these parameters do not have a physical representation as showed later.

Therefore, the no-normalized posterior probability can be calculated as $$P(\Theta \mid D, M) \propto \prod_{j=1}^{n} \exp\left(-\frac{1}{2}\left(\frac{u_{AE_j}^{id} - u_{AE_j}^{cp}(\Phi, B, q) - \varepsilon_j}{\sigma_j^{u_{AE}}}\right)^2\right) U(\Theta) \quad (15)$$

where $U(\Theta)$ is the uniform distribution in a region where the parameters $\Theta$ are feasible (within lower and upper bounds), reducing significantly the region of integration.

The framework of the present disclosure uses Bayesian inference to gain knowledge on the value of the parameters, $\Theta$ when AE data and number of cycles are obtained. These updating parameters $\Theta=[\Phi,B,q,\epsilon]$ correspond to a total of 6 and 7 variables when the models in Eqn. (11) and Eqn. (12) are used respectively.

The predictive probability distribution of the range of stress intensity factor range $\widehat{\Delta K}$, at some number of cycles N, is obtained applying the total probability theorem $$P(\widehat{\Delta K} \mid D,N,M) = \int_{s(\Theta)} P(\widehat{\Delta K} \mid \Theta,D,N,M) P(\Theta \mid D,M) d\Theta \quad (16)$$

where $P(\widehat{\Delta K} \mid D,N,M)$ is the predictive probability distribution of the stress intensity factor range, $P(\Theta \mid D,M)$ is the posterior from Eq. (15), $P(\widehat{\Delta K} \mid \Theta,D,N,M)$ is the probability of $\widehat{\Delta K}$ for a given $\Theta$, D, N and M. Given the mathematical complexity of the terms $P(\Theta \mid D,M)$ and $P(\widehat{\Delta K} \mid \Theta,D,N,M)$, it is difficult to obtain an analytical solution of the integral in Eq. (16). Therefore, a numerical solution is obtained by using a Monte Carlo method. The fatigue life of the structural element is forecasted by sampling the posterior distribution in Eqn. (15) and then computing the stress intensity factor range from Eqn. (7) using these samples. Once the predicted probability distribution of the stress intensity factor range at a given number of cycles is known, the probability of failure ($P_{failure}$) can be calculated as $$P_{failure} = P(\Delta K > \Delta K_{cr}) \quad (17)$$

where $\Delta K_{cr}$ is a critical stress intensity factor range.

The present disclosure utilizes a Markov Chain Monte Carlo (MCMC) method, the Metropolis-Hastings algorithm to sample from the posterior distribution. This algorithm creates a Markov chain where a proposed sample $\Theta^{t+1}$ depends on the previous sample $\Theta^t$. Every candidate $\Theta^{t+1}$ is obtained from the distribution $q(\Theta^{t+1},\Theta^t)$ and has a probability of shifting from $\Theta^t$ to $\Theta^{t+1}$ given by $$\lambda(\Theta^t, \Theta^{t+1}) = \min\left\{\frac{P(\Theta^{t+1} \mid D, M) q(\Theta^{t+1}, \Theta^t)}{P(\Theta^t \mid D, M) q(\Theta^t, \Theta^{t+1})}, 1\right\} \quad (18)$$

if $P(\Theta^t \mid D,M)$ $q(\Theta^t,\Theta^{t+1}) > 0$, otherwise 1. Notice that the term $P(\Theta \mid D,M)$ is present in both: numerator and denominator, then the joint distribution $P(\Theta \mid D, M)$ does not need to be normalized, which is advantageous when dealing with posterior distributions that otherwise require integration. The distribution $q(\Theta^{t+1},\Theta^t)$ is chosen here as $q(\Theta^{t+1},\Theta^t)$, where $q(\bullet)$ is a multivariable Gaussian distribution. Resulting in the random walk represented by $\Theta^{t+1}=\Theta^t+z$, where z is aleatory and follows $q(\bullet)$.

It is challenging to sample from a multivariable probability distribution such as the one in Eqn. (15). Depending upon the complexity of the numerical model and the quality of the experimental data, it is possible for these probability distributions to have very large flat regions of zero probability and small regions with multiple maxima that are narrowed and peaked. Therefore, finding a starting point $\Theta^0$ for the sampling algorithm is not straight forward procedure and may involve using an optimization algorithm to find such regions of maximum probability. Furthermore, the random walk can stay localized in a small region close to the starting point $\Theta^0$ and move very slowly to other regions of larger probability. For solving this issue an initial portion of the samples are discarded and several runs with different starting points are performed. Convergence is monitored based on criteria in which the variance between chains and within chains is calculated respectively as $$B_\theta = \frac{1}{\zeta(\psi-1)} \sum_{\lambda=1}^{\psi} \left(\sum_{i=1}^{\zeta} \theta_{i\lambda} - \frac{1}{\psi}\sum_{\lambda=1}^{\psi}\sum_{i=1}^{\zeta} \theta_{i\lambda}\right)^2 \quad (19)$$

$$W_\theta = \frac{1}{\psi(\zeta-1)} \sum_{\lambda=1}^{\psi} \sum_{i=1}^{\zeta} \left(\theta_{i\lambda} - \frac{1}{\zeta}\sum_{i=1}^{\zeta} \theta_{i\lambda}\right)^2 \quad (20)$$

where, $\psi$, is the number of chain sequences and $\xi$, the number of samples per sequence. Then the potential scale reduction, $\widehat{R}_\theta$ is estimated as $$\widehat{R}_\Theta = \sqrt{\frac{\frac{\zeta-1}{\zeta}W_\Theta + \frac{1}{\zeta}B_\Theta}{W_\Theta}}. \quad (21)$$

The potential scale reduction converges to 1 as $\xi$ goes to infinity. More samples are needed if the potential scale reduction is high. Once the sample points are obtained, the parameters $\Theta$ are used to predict the stress intensity factor at a given number of cycles.

Similar to any MCMC methodology the crack growth monitoring framework of the present disclosure requires the evaluation of a set of equations millions of times. This makes the algorithms computationally expensive, but possible to parallelize. A distributed computing strategy with a cluster of 200 cores was used to run the framework of the present disclosure. Every core continually ran the job of obtaining chains of a specific number of samples, which were placed together by a submitter machine that read the results from these jobs and evaluated the stopping criterion. The Bayesian inference algorithms and the sampling algorithm that obtained each chain were programmed in language C, while the submitter machine that submitted, read results and evaluated the stopping criterion was programmed in Matlab. This approach allows the application of the crack growth monitoring framework of the present disclosure in an almost real-time fashion.

The following examples are meant to illustrate the disclosure described herein and are not intended to limit the scope of this disclosure.

EXAMPLES

Figure 2:
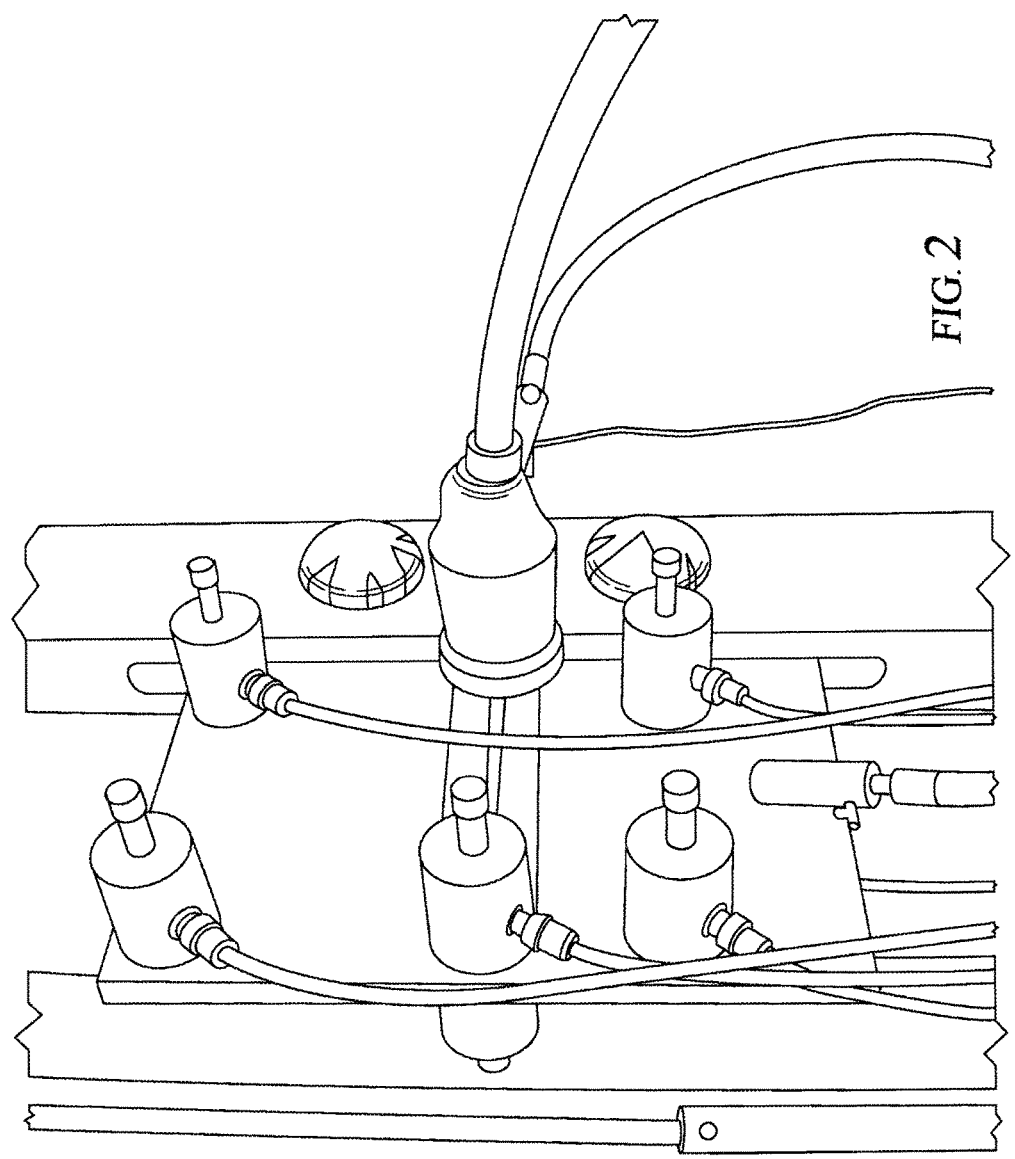
FIG. 2 illustrates a specimen mounted at the MTS machine in accordance with certain aspects of the present disclosure.

The methodology described herein was validated using experimental data from four compact tension (CT) specimens with the same geometry (FIG. 1). The CT specimens had a thickness of 19.1 mm and were made of steel A572 grade 50. Fatigue tests were performed using cyclic tension loads with the minimum and maximum loads shown in Table 1 at a frequency of 1 Hz. The cyclic load was applied using load controlled mode through a servo hydraulic mechanical testing machine (810 Material Test System). FIG. 2 shows the first CT specimen mounted at the MTS machine during the cyclic test. Surface cracks were monitored optically using a high resolution microscope and through AE signals obtained with instruments manufactured by Mistras Group. The pulses from crack initiation and propagation were captured using five standard resonant transducers of type R15I-AST with integrated preamplifier of 40 dB. The location of the transducers at the specimens is depicted in FIG. 1 and FIG. 2. The transducers were attached to the specimen using vacuum grease. The AE data was processed and displayed through a 16-channel Sensor Highway II-Remote Asset Integrity Monitor system. AE signals were filtered using a pass band filter from 100 kHz to 1 MHz. Pencil lead break tests (ASTM 1994) were performed before and after each loading test to check the performance of the transducers and obtain reference waveforms.

Noise caused by friction at the pins and crack surfaces was reduced by using prevention and a trigger threshold. Prevention was performed grapping the pins with cloth and filling the gaps with plastic shims. The triggering threshold was obtained by characterizing the noise with verification tests, which was performed at a load level at which the crack did not grow to guarantee that all the acoustic emission events were caused by friction emission. Then, a threshold of 45 dB was fixed to trigger the AE channel and a Swansong filter was applied. Additional information about the test procedures, data analysis and filtering techniques is described in Yu, J., P. Ziehl, Zarate, B., and Caicedo, J. (2011), "Prediction of Fatigue Crack Growth in Steel Bridge Components using Acoustic Emission." *Journal of Constructional Steel Research*, incorporated by reference herein.

The methodology of the present disclosure was validated using the crack length measurements from the fatigue test. FIG. 3 to FIG. 6 shows the AE cumulative energy and the measured crack length versus the number of cycles for all CT specimens. The crack growth monitoring framework of the present disclosure only uses AE data to update the numerical models and estimate a stress intensity factor range. Crack length is used to calculate the stress intensity factor range, for validation purposes, as described in Dowling, N. (2007), "Mechanical behavior of materials: engineering methods for deformation, fracture, and fatigue" Fracture of cracked members, Upper Saddle River, Pearson Prentice Hall, 331, incorporated by reference herein. FIG. 7 shows the rates of crack length and AE energy versus the stress intensity factor range for CT1. This log-log plot shows a linear trend in the scattered data of the rates of crack length and absolute energy. The scattering in the data can be used as indicator of the uncertainty on the measurements, showing that the uncertainty on the absolute energy measurements which has a coefficient of determination 0.2 (FIG. 7) is larger than that of the crack length measurements with a coefficient of determination 0.7. Similar results are found for the other CT specimens. FIG. 8 shows the stress intensity factor range versus the absolute AE energy for CT1. The measured data was obtained using the measured crack length and the theoretical equation for the stress intensity factor range for a CT specimen (Eqn. (8)) while the other lines were obtained using Eqn. (11) and Eqn. (12). The described models provide a good approximation for the measured data. Similar plots were found for the other CT specimens.

The framework described herein was used to predict the stress intensity factor range at different number of cycles using the models of Eqn. (11) to Eqn. (12) as a function of AE data only. Data from the first part of the test was used to feed the technique and predict the stress intensity range for the remaining of the test (until stage III is reached). The amount of data used for updating depends on the CT specimen since each specimen reached stage III at a different number of cycles. Data from the first 10000 cycles was used for CT1, 14000 cycles for CT2, 22000 cycles for CT3 and 89000 cycles for CT4. The mean value of the AE cumulative absolute energy presented in FIG. 3 to FIG. 6 was used to update and determine the probability distribution of the material and stress intensity factor range model parameters (Eqn. (11) to Eqn. (12)). A standard deviation of 10% of the mean values of the AE data was assumed in the formulation of the posterior probability distribution $\sigma_j^{\mu_{AE}}$ on Eqn. (14). FIG. 9 shows the marginal distribution of the parameter $\phi_1$ which corresponds physically to the stress intensity factor range at the moment at which the sensors were deployed for CT1. Notice that the mean value of $\phi_1$ for Eqn. (11) and Eqn. (12) is approximately 62 Mpa$\sqrt{m}$. FIG. 10 shows the marginal distributions of $\epsilon$ when models of Eqn. (11) and Eqn. (12) are used for specimen CT1. These parameters correspond to the error between the numerical model and the experimental data for both models, and are useful for detecting model inadequacy. FIG. 10 shows that both models have a small error (maximum of about 2%) centered at zero. FIG. 11 shows the marginal distribution of the material constant, q (Eqn. (6)) using the models of Eqn. (11) and Eqn. (12). Both models have a similar mean for the material constant around 4.85. Table 2 shows the number of samples needed to meet the stopping criteria of the MCMC and the total computational time (measured by the submitter machine) needed to acquire these samples for CT1. As it was expected Table 2 shows that increasing the complexity and the number of variables of the numerical model increases the number of samples needed to have a good representation of the posterior distribution and the computational time. That is, the model of Eqn. (12) is more complex than the model of Eqn. (11) and therefore requires more sample points and a larger computational time. Similar results for the marginal probability distributions and computational time were found for the other CT specimens.

FIG. 12 to FIG. 15 show the stress intensity factor range predicted for the different CT specimens using the proposed models. The prognosis is presented as 99% confidence intervals. The models predict accurately the measured stress intensity factor range. However, the predicted confidence intervals get larger as the prediction gets further away in the future. The excessive increase in the uncertainty of the prediction serves as an indicator that the fracture mechanics model is not appropriate for the current state of the crack growth. Around the 15000 cycles for CT1 the crack growth rate moves from the stable stage II to the unstable stage III where the prediction model is inadequate. Similar behavior can be observed in FIG. 13 to FIG. 15 for the additional specimens.

Table 3 shows the predicted probability of failure at different number of cycles using the proposed models. The probability of failure was calculated using a critical stress intensity factor range of 90 MPa $\sqrt{m}$ for CT1 which had a high load range, and 45 MPa $\sqrt{m}$ for the other CT specimens which had significantly lower load range (Table 1). Small differences can be found between the models of Eqn. (11) and Eqn. (12) at the beginning of the prediction. The model of Eqn. (11) shows a continuous increase in the probability of failure of the specimen as the number of cycles increases. On the other hand the model of Eqn. (12) shows and odd behavior once the crack enters the stage III for CT1 in which the probability of failure at 16000 cycles is lower than at 15000 cycles. This is a clear indication that the model is unreliable after the 15000 cycles. In addition, the results for CT2 and CT4 using Eqn. (12) did not converge at the highest number of cycles. This behavior is expected because the specimen is entering stage III and the models do not apply (Eqn. (5) and Eqn. (6) do not hold. FIG. 16 shows the probability distribution of the predicted stress intensity factor range for CT1 at 16000 cycles for both models of Eqn. (11) and Eqn. (12). Both models are double peaked and the prognosis could be improved if a prior distribution that decreases the probability of the updating parameter region that creates the left peak were applied.

The effect of continuously acquiring additional data on the methodology of the present disclosure was evaluated by running the prediction algorithm with different sets of data for CT1. These simulations were chosen to be run using only the model of Eqn. (11), to take advantage of its lowest computational time and more stable results. FIG. 17 shows the prognosis using data from 0 to 10000 cycles, then the data was increased an additional 1000 cycles for a total of 5 sets of data. The uncertainty of the prognosis may increase or decrease as additional data is gathered depending upon the quality of the new data. For instance, compare the size of the intervals for the set of data up to 10000 cycles with the set of data up to 12000 cycles. This shows that even if AE data from early crack stages is not available the prognosis of the framework of the present disclosure will improve as additional AE data is obtained if the quality of the incoming data is high.

The present disclosure presents the formulation and validation of a probabilistic crack growth monitoring framework applicable to structural elements subjected to cyclic loading using acoustic emission data. The framework predicts the probability distribution of the stress intensity factor range at different number of cycles during stable crack growth. The predicted stress intensity factor range is used to infer the probability of failure of a structural element. The methodology assumes the stress intensity factor range as a polynomial equation, which is function of the energy of the AE signal. The coefficients of the polynomial, material constants and modeling error are considered updating variables and are treated as random variables. The joint probability distribution of these updating variables is estimated through Bayesian inference using the absolute energy of the AE signal obtained from the element. Then, the stress intensity factor range prediction is calculated through a Markov Chain Monte Carlo method that runs in a computer cluster.

The framework of the present disclosure was validated using experimental data from four fatigue test in Compact Tension specimens. Acoustic emission and crack length data were obtained from the tests. A portion of the AE data was used to feed the methodology and the crack length data was used to validate the predictions performed by the methodology. Results show that the methodology can successfully estimate the stress intensity factor range probability density function at different number of cycles ahead in the future. The robustness of the methodology was evaluated by using incomplete sets of data where a portion of the data from an early stage of the test was missing. Results show that the initial uncertainty caused by the lack of the earlier data could be reduced as additional data was obtained.

Results from the experimental validation show that the framework described herein was successful at predicting the crack growth in CT specimens subjected to fatigue under constant amplitude. Experimental stress intensity factor range falls within the 99% confidence interval given by the methodology for all specimens tested. The only data required by the technique are the AE and its corresponded number of cycles. The present disclosure has the potential for field applications because knowledge of the pristine condition, the initial crack length of the structural element, load amplitude, and specific steel material AE properties are not required.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed is:

1. A method of using acoustic emission data to predict the state of a structural element, the method comprising:
   capturing, by one or more acoustic emission sensors coupled to a structural element, acoustic emission data for the structural element, wherein the acoustic emission data comprises an absolute energy value of the acoustic emission from the structural element;
   predicting, by one or more computing devices, a future stress intensity in the structural element using the captured acoustic emission data, wherein the future stress intensity is correlated probabilistically from the absolute energy value of the acoustic emission data using a predictive probability distribution model;
   sampling, by the one or more computing devices, the predictive probability distribution model to calculate the probability of future failure of the structural element using the predicted future stress intensity; and
   providing one or more of the future stress intensity and the probability of future failure as output to a user.

2. The method as in claim 1, further comprising utilizing a Bayesian inference model to predict the future stress intensity in the structural element using the captured acoustic emission data.

3. The method as in claim 1, further comprising utilizing a Markov Chain Monte Carlo model to sample the predictive probability distribution model.

4. The method as in claim 1, further comprising capturing additional acoustic emission data.

5. The method as in claim 1, wherein the future stress intensity is a function of the acoustic emission data.

6. The method as in claim 1, further comprising applying a filtering technique.

7. The method as in claim 1, wherein the structural element is subjected to fatigue at a constant load amplitude.

8. The method as in claim 1, wherein the captured acoustic emission data comprises its corresponded number of cycles.

9. The method as in claim 1, wherein the structural element is a bridge.

10. The method as in claim 1, wherein the structural element is a load bearing member.

11. A system for predicting the state of a structural element with acoustic emission data, the system comprising:
a sensor coupled to a structural element for capturing acoustic emission data from the structural element, wherein the acoustic emission data comprises an absolute energy value of the acoustic emission from the structural element; and
a processor, the processor configured to utilize captured acoustic emission data from the sensor to predict a future stress intensity in the structural element, wherein the future stress intensity is correlated probabilistically from the absolute energy value of the acoustic emission data using a predictive probability distribution model, sample the predictive probability distribution model to calculate the probability of future failure of the structural element using the predicted future stress intensity, and provide one or more of the future stress intensity and the probability of future failure as output to a user.

12. The system as in claim 11, wherein the processor utilizes a Bayesian inference model to predict the future stress intensity in a structural element using its captured acoustic emission data.

13. The system as in claim 11, wherein the processor utilizes a Markov Chain Monte Carlo model to sample the predictive probability distribution model.

14. The system as in claim 11, wherein the sensor is configured to capture additional acoustic emission data after an initial capture.

15. The system as in claim 11, wherein the future stress intensity is a function of the acoustic emission data.

16. The system as in claim 11, further comprising a filtering element configured to apply a filtering technique.

17. The system as in claim 11, wherein the system is configured to test a structural element that is subjected to fatigue at a constant load amplitude.

18. The system as in claim 11, wherein the sensor is configured to capture a corresponded number of cycles of the acoustic data.

19. The system as in claim 11, wherein the system is configured to test a structural element comprising a bridge.

20. The system as in claim 11, wherein the system is configured to test a structural element comprising a load bearing member.

* * * * *